_United States Patent_ [19]

Findlay et al.

[11] Patent Number: 4,621,094

[45] Date of Patent: Nov. 4, 1986

[54] ANTI-HISTAMINIC PYRIDYL COMPOUNDS

[76] Inventors: John W. A. Findlay, Rte. 2, Box 514, Chapel Hill, N.C. 27514; Geoffrey G. Coker, No. 80 Pickhurst Park, Bromley, England

[21] Appl. No.: 683,333

[22] Filed: Dec. 19, 1984

Related U.S. Application Data

[63] Continuation of Ser. No. 474,728, Mar. 10, 1983, abandoned.

[51] Int. Cl.$^4$ ............... A61K 31/44; C07D 213/55
[52] U.S. Cl. ........................... 514/357; 514/161; 514/282; 546/333
[58] Field of Search ............... 546/333; 514/161, 282, 514/357

[56] References Cited

U.S. PATENT DOCUMENTS

| | | | |
|---|---|---|---|
| 2,567,245 | 9/1951 | Sperber et al. | 546/333 |
| 3,862,173 | 1/1975 | Carr et al. | 546/237 |
| 4,355,036 | 10/1982 | Villani et al. | 424/267 |

FOREIGN PATENT DOCUMENTS

| | | |
|---|---|---|
| 1227464 | 10/1966 | Fed. Rep. of Germany . |
| 2349493 | 4/1974 | Fed. Rep. of Germany . |
| 41061 | 12/1972 | Israel . |
| 807757 | 1/1959 | United Kingdom . |
| 1440777 | 6/1976 | United Kingdom . |

OTHER PUBLICATIONS

Burger, Medicinal Chem., J. Wiley, 3rd Edition, p. 76.
Kuntzman et al., Chem. Ab., vol. 71, Jul. 1969, 11415f.
Hucker et al., Drug Metabolism and Disposition, vol. 9 (5), pp. 428–433.
Buzas, J. Med. Chem., vol. 23, pp. 149–153 (1980).
Findlay et al., Aspet, May 16, 1980.
Physicians Desk Ref. (1978), pp. 707 and 708 Actidil and Actifed.
Kuntzman et al., Chem. Abstracts, vol. 71, 11415f (1969).

_Primary Examiner_—Henry R. Jiles
_Assistant Examiner_—Bernard I. Dentz
_Attorney, Agent, or Firm_—Donald Brown

[57] ABSTRACT

This disclosure describes compounds of formula I.

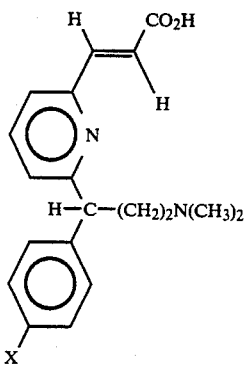

wherein X is Cl or Br (including their pharmaceutically acceptable salts and esters) which have potent antihistamine activity and which are substantially free from sedative effects.

26 Claims, No Drawings

ANTI-HISTAMINIC PYRIDYL COMPOUNDS

This application is a continuation of application Ser. No. 474,728 filed 3/15/83 now abandoned.

The present invention relates to new chemical compounds exhibiting antihistamine activity, to processes for preparing them, to novel intermediates involved in their preparation, to pharmaceutical compositions containing them and to their use in medicine.

U.S. Pat. No. 2,567,245 discloses a group of pyridyl aliphatic amines with antihistamine activity and specifically discloses 3-(4-bromophenyl)-3-(2-pyridyl)-N,N-dimethylpropylamine and 3-(4-chlorophenyl)-3-(2-pyridyl)-N,N-dimethylpropylamine which are hereinafter referred to by their generic names bromopheniramine and chlorpheniramine respectively or collectively as the pheniramines. The pheniramines have gained widespread clinical acceptance and are the most common antihistamines on the market. However, like all other potent antihistamines in clinical use they produce sedation and drowsiness in varying degrees in most patients (L. Goodman and A. Gilman, *The Pharmacological Basis of Therapeutics*, 4th ed., p. 640, Macmillan, New York, 1970). This sedating effect limits the use of antihistamines by patients who must operate machinery, drive motor vehicles or must engage in activities requiring mental alertness.

The antihistamines now in use, eg. diphenhydramine, the pheniramines, pyrilamine, promethazine and triprolidine, exhibit varying degrees of anticholinergic activity. Such activity causes dryness of mouth, blurred vision and tachycardia and is generally regarded as undesirable. Two novel compounds having potent antihistamine activity which are substantially free from sedative effects, and which have little or no anticholinergic effect have now been discovered.

Accordingly this invention provides the compounds of formula (I)

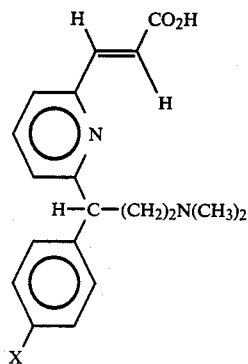

wherein X is Cl or Br
which are named: when X is Cl, (E)-6-[1-(4-chlorophenyl)-3-dimethylamino propyl]-2-pyridyl acrylic acid, or when X is Br, (E)-6-[1-(4-bromophenyl)-3-dimethylamino propyl]-2-pyridyl acrylic acid.

This invention also includes pharmaceutically acceptable esters as well as acid addition salts and salts of the carboxylic acid group of the compounds of formula (I).

If the acrylic acid side chain is placed in any position on the pyridine ring other than that shown in FIG. 1 (i.e., the 2 position) or the length of the side chain is increased to more than three carbons, the antihistaminic activity of such a compound is significantly reduced relative to the compound of formula (I).

1. A method for preparing the compounds of formula (I) comprises reacting a compound of formula (II)

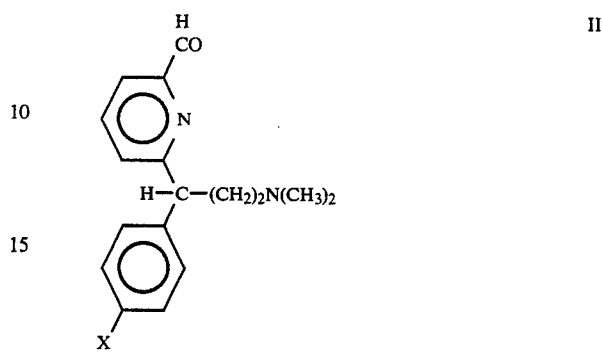

wherein X is as defined for formula (I) with the sodium salt of triethylphosphonacetate in dry toluene.

In turn the compounds of formula (II) may be prepared by reacting a compound of formula (III)

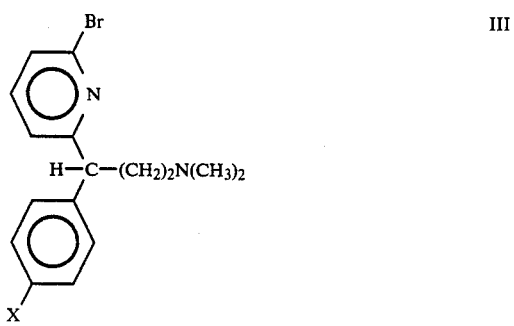

with n-butyllithium in dry tetrahydrofuran then treatment with N,N-dimethylformamide followed by treatment with water.

Compounds of formula III can be synthesized by reacting a compound of formula IV with a compound of formula (V) by the Wittig method (see *Organic Reactions*, 14, 270–490 (1965) and *Pure and Applied Chemistry*, 9, 245–254 (1964))

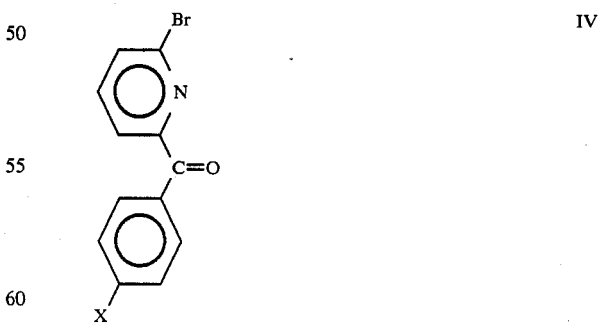

wherein X is Cl or Br and $R^1$ is lower alkyl or phenyl followed by reduction of the resulting double bond by methods of the art such as catalytic hydrogenation.

The compound of formula (V) is a Wittig reagent which may be prepared by treatment of a phosphonium salt (VI) with a strong base, for example an alkyl or aryl lithium compound or sodium hydride in a suitable solvent, for example toluene or tetrahydrofuran.

$(R^1)_3P=CHCH_2N(CH_3)_2$  V wherein $R^1$ is as defined above. The phosphonium salts (VI) are prepared by known methods (e.g., see British Pat. No. 1, 161, 201).

The compounds of formula IV may be prepared by 1) reacting 2,6-dibromopyridine with p-halo benzaldehyde in dry ether in the presence of a strong base such as n-butyllithium followed by 2) oxidation of the resulting hydroxy product to the corresponding ketone.

2. Compounds of formula (I) may also be synthesized by reacting compounds of formula (VII)

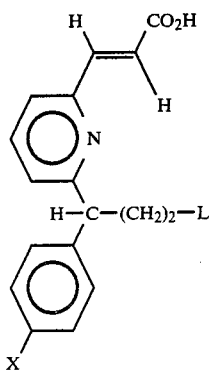

VII wherein L is a leaving group as defined by J. March, *Advanced Organic Chemistry*, 2nd, ed., pages 683 and 895, McGraw Hill, New York, 1977, e.g. —Br, —Cl, toluene sulphonate, etc, and X is Cl or Br.
with dimethyl amine.

3. A further method for synthesis of compound of formula (I) comprises dehydration of compounds of formula (VIII).

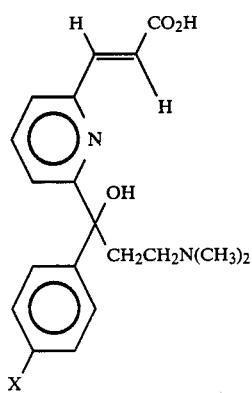

VIII followed by selective reduction of the resulting double bond.

Compounds of this invention have the same utilities as an antihistamine used clinically at present. They bind competitively to the $H_1$ histamine receptor site. They may be used to relieve symptoms of nasal stuffiness due to colds and vasomotor rhinitis and for the symptomatic control of all allergic conditions including nasal allergy, perennial rhinitis, urticaria, angioneurotic oedema, allergic conjunctivitis, food allergy, drug and serum reactions, insect bites and stings and desensitizing reactions. The compounds are also indicated in all conditions responsive to its antipruritic activity including allergic dermatoses, neurodermatitis, anogenital pruritus, and pruritus of non-specific origin such as eczema, and of specific cause such as chickenpox, photosensitivity and sunburn. In contrast to the antihistamines in present use, the compounds of this invention are not sedating and have little or no anticholinergic side effects.

The amount of active compound (defined herein as a compound of formula (I) including esters and pharmaceutically acceptable salts) required for use in the above conditions will vary both with the route of administration, the condition under treatment and the mammal undergoing treatment, and is ultimately at the discretion of the physician. A suitable oral dose of the active compound for a mammal is in the range of from 0.025 to 1.0 mg per kologram body weight per day; preferably from 0.04 to 0.24 mg/kg. For example a typical dose for a human recipient of a compound of formula (I) is 0.12 mg/kg body weight per day.

The desired daily dose is preferably presented as from one to six sub-doses administered at appropriate intervals throughout the day as needed. Where three sub-doses of compounds of formula (I) are employed, each will preferably lie in the range of from 0.014 to 0.08 mg/kg body weight; for example, a typical unit sub-dose (which can be given in a pharmaceutical formulation such as a tablet, capsule or syrup) of the active compound for a human recipient is about 0.25 to 20 mg, typically 2 mg while the typical total daily preferred dose is in the range of 2 to 12 mg. As a syrup the amount would be at a concentration of 0.25 to 20 mg/5 mL of solvent, e.g. water, flavoring, etc.

While it is possible for the active compound previously described to be administered alone as the raw chemical, it is preferable to present the active compound, a compound of formula (I), as a pharmaceutical formulation. Formulations of the present invention, both for veterinary and for human medical use, comprise the active compound together with one or more pharmaceutically acceptable carriers thereof and optionally any other therapeutic ingredients. For example, the active compound may be formulated with a sympathomimetic agent such as the decongestants pseudoephedrine or phenylpropanolamine, an antitussive such as codeine, an analgesic such as acetaminophen, an antiinflammatory and antipyretic such as aspirin, or an expectorant such as guaifenesin. The carrier(s) must be pharmaceutically acceptable in the sense of being compatible with the other ingredients of the formulation and not deleterious to the recipient thereof.

The formulations include those suitable for oral, rectal, topical, nasal, ophthalmic or parenteral (including subcutaneous, intramuscular and intravenous) administration.

The formulations may conveniently be presented in unit dosage form and may be prepared by any of the methods as well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier or both and then, if necessary, shaping the product into the desired formulations.

Formulations of the present invention suitable for oral administration may be presented as discrete units such as capsules, cachets, tablets or lozenges, each containing a predetermined amount of the active compound (defined herein as a compound of formula (I)); as a powder or granules; or a suspension in an aqueous liquid or non-aqueous liquid such as a syrup, an elixir, an emulsion or a draught.

A tablet may be made by compression or molding, optionally with one or more accessory ingredients. Compressed tablets may be prepared by compressing in a suitable machine, with the active compound being in a free-flowing form such as a powder or granules which is optionally mixed with a binder, disintegrant, lubricant, inert diluent, surface active agent or dispersing agent. Molded tablets comprised of a mixture of the powdered active compound with any suitable carrier may be made by molding in a suitable machine.

A syrup may be made by adding the active compound to a concentrated, aqueous solution of a sugar for example sucrose to which may also be added any accessory ingredient(s). Such accessory ingredient(s) may include flavourings, an agent to retard crystallization of the sugar or an agent to increase the solubility of any other ingredient, such as a polyhydric alcohol for example, glycerol or sorbitol, and suitable preservatives.

Formulations for rectal administration may be presented as a suppository with a usual carrier such as cocoa butter, or hydrogenated fats or hydrogenated fatty carboxylic acids.

Formulations suitable for parenteral administration conveniently comprise a sterile aqueous preparation of the active compound which is preferably isotonic with the blood of the recipient.

Nasal spray formulations comprise purified aqueous solutions of the active compound with preservative agents and isotonic agents. Such formulations are adjusted to a pH and isotonic state compatible with the nasal mucous membranes.

Ophthalmic formulations are prepared by a similar method to the nasal spray except the pH and isotonic factors are adjusted to match that of the eye.

Topical formulations comprise the active compound dissolved or suspended in media such as mineral oil, petrolatum, polyhydroxy alcohols or other bases used for topical pharmaceutical formulations. The addition of other accessory ingredients, vide infra, may be desirable.

In addition to the aforementioned ingredients, the formulations of this invention may further include one or more accessory ingredient(s) selected from diluents, buffers, flavouring agents, binders, disintegrants, surface active agents, thickeners, lubricants, preservatives (including antioxidants) and the like.

When used in medicine, the salts of the compound of formula (I) should be both pharmacologically and pharmaceutically acceptable, but non pharmaceutically acceptable salts may conveniently be used to prepare the free active compound or pharmaceutically acceptable salts thereof and are not excluded from the scope of this invention. Such pharmacologically and pharmaceutically acceptable salts include, but are not limited to, those prepared from the following acids: hydrochloric, hydrobromic, sulfuric, nitric, phosphoric, maleic salicylic, p-toluenesulfonic, tartaric, citric, methanesulfonic, formic, malonic, succinic, naphthalene-2-sulfonic and benzenesulfonic. Also pharmaceutically acceptable salts can be prepared as alkaline metal or alkaline earth salts, such as sodium, potassium or calcium salts of the carboxylic acid group. The esters may be, for example, the methyl, ethyl, propyl, or butyl.

The following Examples are provided by the way of illustration of the present invention and should in no way be construed as a limitation thereof. All temperature indicated are in degrees Celsius.

EXAMPLE 1

(E)-6-(1-(4-chlorophenyl)-3-dimethylaminopropyl)-2-pyridyl acrylic acid

A. α-(6-Bromo-2-pyridyl)-4-chlorobenzyl alcohol

To a stirred solution of 2,6-dibromopyridine (100 g) in dry ether (1 l) under nitrogen at $-70°$ was added dropwise during 2 hr a solution of n-butyllithium (270 mL, 1.7M in hexane). After an additional 0.5 hr, a solution of p-chlorobenzaldehyde (65 g) in dry ether (500 mL) was added during a 1 hr period. The reaction mixture was allowed to warm to ca. 0° and then poured into aqueous hydrochloric acid (1 l, 4N). The ether layer was separated and the aqueous layer was extracted with two additional portions (300 mL) of ether. The combined ether layers were washed with water (500 mL), dried ($Na_2SO_4$) and concentrated to give a syrup. The crude product was chromatographed on silica gel using the Waters Prep 500 (trademark of Waters Associates Inc., Milford, MA 01757) with methylene chloride to provide α-(6-bromo-2-pyridyl)-4-chlorobenzyl alcohol (93.8 g), m.p. 64.5°–65°.

Analysis Calcd for $C_{12}H_9BrClNO$: C, 3.04; N, 4.69. Found: C, 48.32; H, 3.05; N, 4.67.

B. 2-Bromo-6-(4-chlorobenzoyl)pyridine

The benzhydrol (88 g) prepared above was dissolved in methylene chloride (400 mL) and added to a stirred suspension of pyridinium chlorochromate (120 g) in methylene chloride (500 mL). After 22 hr the solvent was decanted and the residual sludge was washed with four portions (250 mL) of ether. The combined organic layers were filtered through Florisil (500 g) and evaporated. The fluffy solid residue (78.6 g) was recrystallized from hexane-methylene chloride to provide 2-bromo-6-(4-chlorobenzoyl)pyridine (71.8 g), m.p. 83.5°–84°.

Analysis Calcd. for $C_{12}H_7BrClNO$: C, 48.60; H, 4.72; N, 2.38; Cl, 11.96; Br, 26.95. Found: C, 48.70; H, 4.68; N, 2.44; Cl, 11.92; Br, 26.87.

C. (Z)-2-Bromo-6-(1-(4-chlorophenyl)-3-dimethylaminoallyl)pyridine

A solution of n-butyllithium (60 mL, 1.55M in hexane) was added dropwise during 45 min to a stirred suspension of (2-dimethylaminoethyl)triphenylphosphonium bromide (38.1 g) in dry tetrahydrofuran (500 mL) under nitrogen. After an additional hour at room temperature, a solution of 2-bromo-6-(4-chlorobenzoyl)pyridine (27.3 g) in dry tetrahydrofuran (200 mL) was added dropwise. The mixture was stirred at room temperature for 20 min, then refluxed for 80 min, cooled to room temperature, and poured into water (500 mL). The ether layer was separated and the aqueous phase extracted with three additional portions of ether. The ether layers were combined, washed once with water, dried ($MgSO_4$) and evaporated to give an oil which was triturated with hexane (500 mL). The hexane layer was decanted and concentrated to give a crude mixture of isomeric Z and E alkenes which were separated by chromatography (Waters Prep 500) on silica gel with 95:5/methylene chloride: methanol (E, 7.53 g; Z, 15.19 g). The individual isomers were then rechromatographed on silica gel with ethyl acetate to yield (Z)-2-bromo-6-(1-(4-chlorophenyl)-3-dimethylaminoallyl)- pyridine, m.p. 56°–62°, and (E)-2-bromo-6-(1-(4-chlorophenyl-3-diomethylaminoallyl)pyridine, 69°–70°.

Analysis Calcd. for $C_{16}H_{16}BrClN_2$: C, 54.64; H, 7.97; N, 4.59; Cl, 10.08; Br, 22.73. Found For (Z): C, 54.71; H, 7.99; N, 4.56; Cl, 10.07; Br, 22.69. Found for (E): C, 54.55; H, 7.99; N, 4.56, Cl, 10.10; Br, 22.78.

D. 2-Bromo-6-(1-(4-chlorophenyl)-3-dimethylaminopropyl)pyridine

A solution of E-2-bromo-6-(1-(4-chlorophenyl)-3-dimethylaminoallyl)pyridine (vide supra (2.0 g) in absolute ethanol (150 mL) was stirred under hydrogen with 10% Pt/C (0.86 g) for 48 hr. The reaction mixture was filtered through Celite and the reduction continued with fresh catalyst (0.67 g) for an additional 96 hr. Filtration through Celite and concentration under reduced pressure gave an oil which was chromatographed on silica gel (Waters Prep 500) with 3:1/methanol:methylene chloride. This provided 2-bromo-6-(1-(4-chlorophenyl)-3-dimethylaminopropyl)pyridine (0.66 g) as an oil:TLC Rf 0.22 (silica gel, methanol).

Analysis Calcd. for $C_{16}H_{18}BrClN_2$: C, 54.33; H, 5.13; N, 7.92; Br, 22.60; Cl, 10.02. Found: C, 54.22; H, 5.17; N, 7.89; Br, 22.51; Cl, 9.99.

E. 6-(1-(4-Chlorophenyl)-3-dimethylaminopropyl)-2-pyridine carboxaldehyde

To a cold (−70°) solution of 2-bromo-6-(1-(4-chlorophenyl)-3-dimethylaminopropyl)pyridine (1.44 g) under nitrogen in dry tetrahydrofuran (50 mL) was added with stirring a solution of n-butyllithium (2.4 mL, 1.7M in hexane). After an additional 5 min at −70°, dry dimethylformamide (1.5 mL) was added dropwise during 2 min. The solution was allowed to warm and then quenched with water (5 mL). The solvents were removed under reduced pressure and the residue was dissolved in methylene chloride (50 mL). This solution was extracted with water (3×25 mL), dried ($Na_2SO_4$), and concentrated to give crude 6-(1-(4-chlorophenyl)-3-dimethylaminopropyl)2-pyridine carboxaldehyde (formyl proton δ 10.05, 60 MHz, $CDCl_3$) which was chromatographed on reverse phase ($C_{18}$, Waters Prep 500, 60:40/acetonitrile:water, $K^1=6.3$ ($C_{18}$; 70:30/acetonitrile:water).

F. (E)-6-(1-(4-Chlorophenyl)-3-dimethylaminopropyl)-2-pyridyl acrylic acid

The aldehyde prepared above was reacted with the sodium salt of triethylphosphonoacetate. Ether extraction gave crude ethyl 6-(1-(4-chlorophenyl)-3-dimethylaminopropyl)-2-pyridylacrylate ($K^1=8.3$ on $C_{18}$ with 70:30/acetonitrile:water), NMR (80 MHz, $CDCl_3$) δ 1.32 (t, 3H), 2.15 (m, 10H), 4.25 (m, 3H), 6.75–7.80 (m, 9H). The ester was hydrolyzed with sodium hydroxide (4 equiv) in aqueous methanol. The reaction mixture was neutralized with aqeuous hydrochloric acid (1N) and the solvents removed under reduced pressure. The residue was treated with methanol, filtered, and the methanol removed in vacuo to give the crude acid. Chromatography on reverse phase ($C_{18}$; 40:60/methanol:water) provided (E)-6-(1-(4-chlorophenyl)3-dimethylaminopropyl)-2-pyridyl acrylic acid ($K^1=5.7$ on $C_{18}$ with 30:70/methanol:water) TLC Rf 0.40 (silica gel, methanol); NMR (80 MHz, $CDCl_3$) δ 2.40 (S, 6H), superimposed over 2.0–3.0 (m, 4H), 3.97 (br t, 1H), 6.65–7.70 (m, 9H), 11.5 br s, exchangeable).

EXAMPLE 2

Antihistaminic Activity

The longitudinal muscle was isolated from the intact ileum of guinea pigs (Hartley, male 250–400 g) and placed in an organ bath under 300 mg tension. After one hour of equilibration, cumulative concentration-response curves (Van Rossum, J. M., *Arch. Int. Pharmacodyn. Ther.* 143, 299–330, 1963) to histamine were obtained. Following washing, the tissues were incubated for one hour with the test compound and then a second histamine concentration-response curve was run. Shifts to the right of the agonist concentration-response curve produced by the antagonists were used to construct Schild plots (Arunlakshana, O. And Schild, H. O., *Br. J. Pharmacol:* 14, 48–58, 1959 ). Regression of Log (dr-1) on Log [B], where dr is an equiactive response in the presence and absence of antagonist and [B] is the molar concentration of antagonist, allowed an estimate of $pA_2$, i.e. the negative log of the concentration of antagonist which shifts the control histamine concentration-response curve 2X to the right. The $pA_2$ value for (E)-6-(1-4-chlorophenyl)-3-dimethylaminopropyl)-2-pyridyl acrylic acid was found to be 5.7.

EXAMPLE 3

Formulations

| (A)-Injection | |
|---|---|
| Ingredient | Amount per ampoule |
| Compound of formula (I) | 1.0 mg |
| Water for Injections, q.s. | 1.0 mL |

The finely ground active compound is dissolved in the water for Injections. The solution is filtered and sterilized by autoclaving.

| (B)-Suppository | |
|---|---|
| Ingredient | Amount per suppository |
| Compound of Formula (I) | 1.0 mg |
| Cocoa Butter, or Wecobee ™ Base q.s. | 2.0 g |

Wecobee is a trademark and is a hydrogenated fatty carboxylic acid.

The finely ground active compound is mixed with the melted suppository base (either Cocoa Butter or Wecobee ™ base), poured into molds and allowed to cool to afford the desired suppositories.

| (C)-Syrup | |
|---|---|
| Ingredient | Amount per 5 mL |
| Compound of Formula (I) | 1.0 mg |
| Ethanol | 0.3 mg |
| Sucrose | 2.0 mg |
| Methylparaben | 0.5 mg |
| Sodium Benzoate | 0.5 mg |
| Cherry Flavour | q.s. |
| Coloring | q.s. |
| Water | q.s. to 5.0 mL |

Ethanol, sucrose, sodium benzoate, methylparaben, and flavouring are combined in 70% of the total batch quantity of water. Coloring and the active compound are dissolved in the remaining water, then the two solutions are mixed and clarified by filtration.

| (D)-Tablet | |
|---|---|
| Ingredient | Amount per Tablet |
| Compound of Formula (I) | 1.0 mg |
| Lactose | 110.0 mg |

(D)-Tablet

| Ingredient | Amount per Tablet |
| --- | --- |
| Corn Starch, Pregelatinized | 2.5 mg |
| Potato Starch | 12.0 mg |
| Magnesium stearate | 0.5 mg |

The active compound is finely ground and intimately mixed with the powdered excipients lactose, corn starch, potato starch and magnesium stearate. The formulation is then compressed to afford a tablet weighing 126 mg.

(E)-Capsule

| Ingredient | Amount per Capsule |
| --- | --- |
| Compound of Formula (I) | 1.0 mg |
| Lactose | 440.0 mg |
| Magnesium Stearate | 5.0 |

The finely ground active compound is mixed with the powdered excipients lactose, corn starch and stearic acid and packed into two part, gelatin capsules.

(F)-Tablet

| Ingredient | Amount per Tablet |
| --- | --- |
| Compound of Formula (I) | 1.0 mg |
| Pseudoephedrine HCl | 60.0 mg |
| Lactose | 62.5 mg |
| Potato Starch | 14.0 mg |
| Magnesium Stearate | 1.0 mg |
| Gelatin | 2.8 mg |

A tablet is prepared from the above formulation by the method previously described in Example 7 (D).

(G)-Syrup

| Ingredient | Amount per 5 mL |
| --- | --- |
| Compound of Formula (I) | 1.0 mg |
| Pseudoephedrine HCl | 30.0 mg |
| Codeine Phosphate | 10.0 mg |
| Guaifenesin | 100 mg |
| Methylparaben | 0.5 mg |
| Sodium benzoate | 0.5 mg |
| Flavor | q.s. |
| Color | q.s. |
| Glycerol | 500 mg |
| Sucrose | 2000 mg |
| Purified Water | q.s. to 5.0 mL |

A syrup containing other active ingredients in addition to a compound of formula (I) is prepared from the above ingredients by an analogous method to that described for Example 7 (C) above.

(H)-Nasal Spray

| Ingredient | Amount per 100.0 mL |
| --- | --- |
| Compound of Formula (I) | 1 g |
| Sodium Chloride | 0.8 g |
| Preservative | 0.5 g |
| Purified Water | q.s. 100.0 mL |

The preservative is dissolved in warm purified water and after cooling to 25-30C the sodium chloride and the compound of formula (I) are added. The pH is then adjusted to 5.5-6.5 and purified water was added to bring the final volume to 100.0 mL.

(I)-Ophthalmic Solution

| Ingredient | Amount per 100.0 mL |
| --- | --- |
| Compound of Formula (I) | 0.1 g |
| Sodium Chloride | 0.8 g |
| Preservative | 0.5 g |
| Water for Injection | q.s. 100.0 mL |

This formulation is prepared in a similar way to the nasal spray.

(J)-Topical Cream

| Ingredient | Amount per 100.0 mL |
| --- | --- |
| Compound of Formula (I) | 0.1 g |
| Emulsifying Wax, N.F. | 15.0 g |
| Mineral Oil | 5.0 g |

We claim:
1. A compound of formula (I),

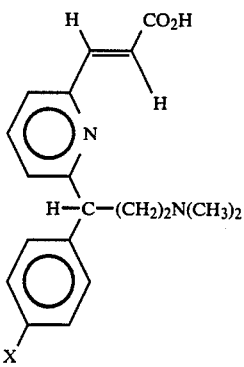

a straight or branched lower alkyl (1-4 carbon atoms) ester, or a pharmaceutically acceptable salt thereof wherein X is Cl or Br.

2. A compound of claim 1 which is (E)-6-[-1-(4-chlorophenyl)-3-dimethylamino propyl]-2-pyridylacrylic acid.

3. A compound of claim 1 which is (E)-6-[1-(4-bromophenyl)-3-dimethylaminopropyl]-2-pyridyl acrylic acid.

4. A compound of claims 1, 2, or 3 as the hydrochloride salt.

5. A method of relieving the detrimental effects of histamine in a mammal comprising administering to said mammal an effective amount of the compound of formula (I),

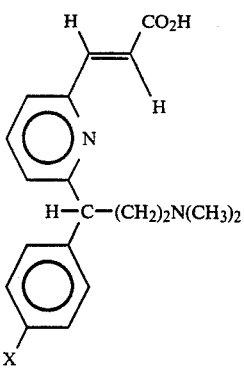

a straight or branched lower alkyl (1–4 carbon atoms) ester, or a pharmaceutically acceptable salt thereof; wherein X is Cl or Br.

6. A method of claim 5 wherein a mammal is a human.

7. A method of claim 5 or claim 6 wherein the compound of formula (I) administered is (E)-6-[1-(4-chlorophenyl)-3-dimethylamino propyl]-2-pyridyl acrylic acid.

8. A method of claim 5 wherein the compound of formula (I) administered is (E)-6[1-(4-bromophenyl)-3-dimethylaminopropyl]-2-pyridyl acrylic acid.

9. A method of relieving in a mammal the detrimental systems of histamine comprising competitively binding the $H_1$ histamine receptor site in the body of said mammal with an effective amount of the compound of formula (I)

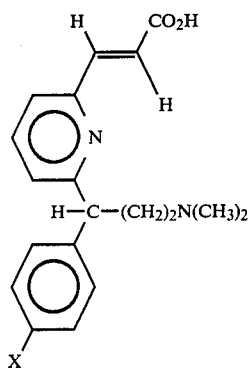

a straight or branched alkyl (1–4 carbon atoms) ester, or a pharmaceutically acceptable salt thereof; wherein X is Cl or Br.

10. A method of claim 9 wherein the mammal is a human.

11. A method of claim 9 or 10 wherein a detrimental symptom is nasal allergy.

12. A method of claim 9 or 10 wherein a detrimental symptom is perennial rhinitis.

13. A method of claim 9 or 10 wherein a detrimental symptom is urticaria.

14. A method of claim 9 or 10 wherein a detrimental symptom is angioneurotic oedema.

15. A method of claim 9 or 10 wherein a detrimental symptom is allergic conjunctivitis.

16. A method of claim 9 or 10 wherein a detrimental symptom is food allergy.

17. A method of claim 9 or 10 wherein a detrimental symptom is drug and serum reactions.

18. A method of claim 9 or 10 wherein a detrimental symptom is insect bites and stings.

19. A method of claim 9 or 10 wherein a detrimental symptom is desensitizing reactions.

20. A anti-histamine pharmaceutical formulation comprising an effective amount of a compound of formula (I)

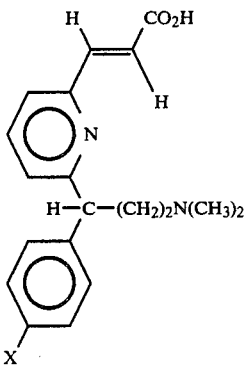

a straight or branched alkyl (1–4 carbon atoms) ester, or a pharmaceutically acceptable salt thereof; wherein X is Cl or Br, together with a pharmaceutically acceptable carrier thereof.

21. A pharmaceutical formulation as claimed in claim 20 in unit dosage form.

22. A pharmaceutical formulation as claimed in claim 20, characterized by being in the form of a tablet, syrup, suppository or sterile aqueous preparation.

23. A pharmaceutical formulation wherein the compound of formula (I) as defined in claim 1 in an effective antihistamine amount is combined with a therapeutic ingredient selected from an effective amount of a sympathomimetic, antitussive or analgesic ingredient or any combination thereof.

24. A pharmaceutical formulation comprising the compound of formula (I) as set forth in claim 1 in an anti-histamine amount in combination with pseudoephedrine or a pharmaceutically acceptable salt thereof.

25. The formulation of claim 24 in which the pharmaceutically acceptable hydrochloride salt of pseudoephedrine is combined with the compound of Formula I.

26. The method of obtaining a combined decongestant and antihistimine effect in a mammal in need thereof comprising the administration of the formulation of claim 24 to a mammal.

* * * * *